United States Patent [19]

Graf

[11] Patent Number: 5,494,530
[45] Date of Patent: Feb. 27, 1996

[54] METHOD OF AND APPARATUS FOR TESTING AND CLEANING OF ENDOSCOPES

[75] Inventor: Marcel Graf, Altishofen, Switzerland

[73] Assignee: F. Gehrig & Co. AG, Ballwil, Switzerland

[21] Appl. No.: 163,871

[22] Filed: Dec. 8, 1993

[51] Int. Cl.⁶ .................................................. B08B 7/04
[52] U.S. Cl. .................. 134/18; 134/22.12; 134/56 R; 134/102.2; 134/113; 134/166 R; 134/168 C; 134/170; 73/40; 73/45.5; 422/112; 422/119; 422/295
[58] Field of Search ................................... 134/18, 22.12, 134/56 R, 113, 102.2, 166 R, 168 C, 170; 73/40, 45.5; 422/112, 119, 295

[56] References Cited

U.S. PATENT DOCUMENTS 5,279,799   1/1994   Moser ................................. 422/292

FOREIGN PATENT DOCUMENTS

| 0089605 | 9/1983 | European Pat. Off. . |
| 0271157 | 6/1988 | European Pat. Off. . |
| 0483059 | 4/1992 | European Pat. Off. . |
| 675064  | 8/1990 | Switzerland . |

Primary Examiner—W. Gary Jones
Assistant Examiner—Sean Vincent
Attorney, Agent, or Firm—Cushman Darby & Cushman

[57] ABSTRACT

In the program-controlled cleaning of endoscopes in a cleaning apparatus, the head parts are cleaned, rinsed, disinfected and rinsed clean in pressure chambers and, at the same time, the insertion tubes are cleaned, rinsed, disinfected and rinsed clean in pipes, attached to these pressure chambers, in a number of cleaning stages using cleaning liquid which is introduced via a circulation pump at a pressure of approximately 200 mbar. Prior to each of these cleaning stages, compressed air generated in the compressed air unit of the cleaning apparatus is introduced from there through the pressure test attachment of each endoscope, which pressure test attachment is connected by means of a pressure test adaptor to a compressed air attachment of the cleaning apparatus, until an internal pressure of 250 mbar is reached. If this pressure is not reached within 5 min or if the internal pressure of the endoscope drops by more than 30 mbar during a subsequent holding time of 30 sec, the circulation pump is not set in operation and the cleaning is discontinued. Otherwise, the internal pressure in the endoscope is kept at 250 mbar during the cleaning stage. The endoscope is tested in this way for leakproofness and is protected from penetration of cleaning liquid, even when a leak occurs during cleaning.

14 Claims, 4 Drawing Sheets

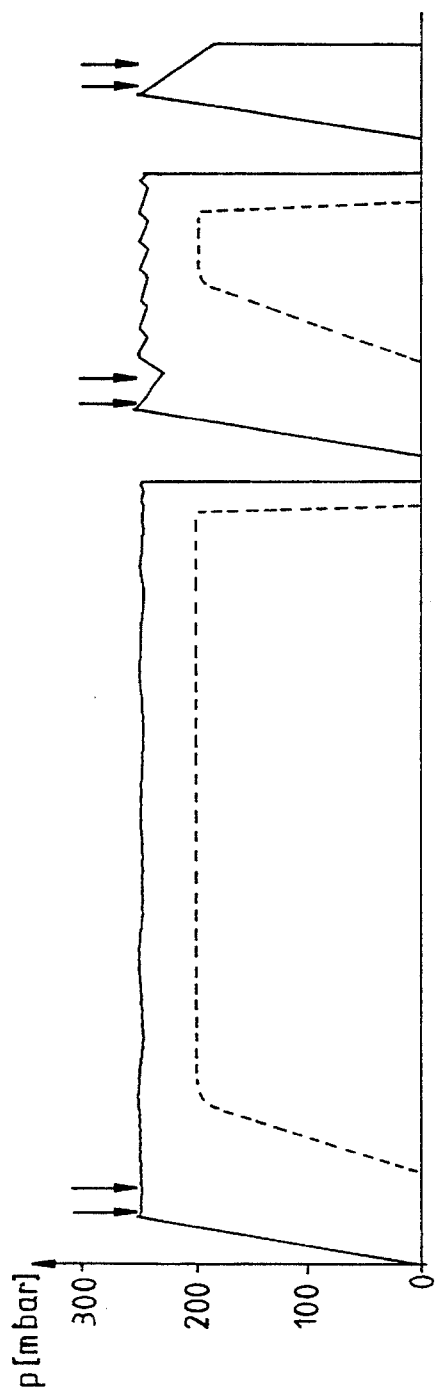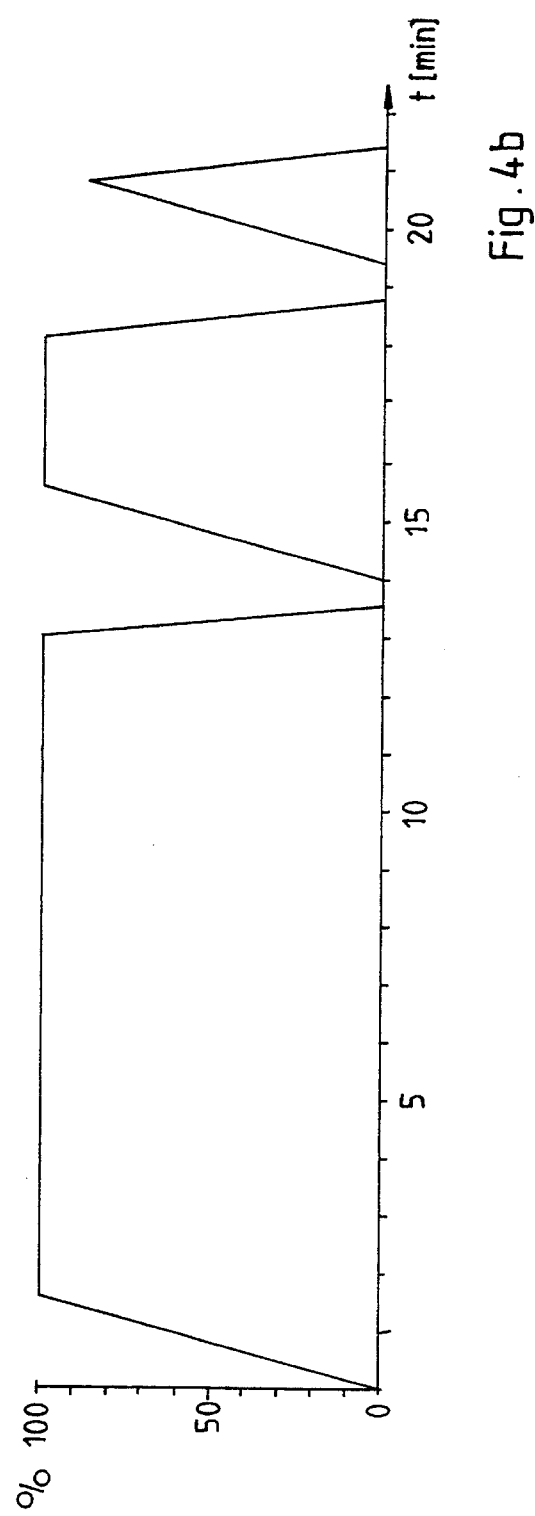

METHOD OF AND APPARATUS FOR TESTING AND CLEANING OF ENDOSCOPES

BACKGROUND OF THE INVENTION

1. Field of the Invention

The invention relates to a method for program-controlled testing and cleaning of endoscopes having a head pan with an attached insertion tube and a pressure test attachment, and to a cleaning apparatus for carrying out testing and cleaning.

2. Description of the Related Art

Endoscopes are used for examining the stomach or intestine and have a head part made of strong material, usually plastic, with an ocular and, usually, one or more attachments and buttons for triggering certain functions of the endoscope, as well as a flexible insertion tube which is attached to the head part and contains, protected by a tubular plastic sheath, a glass fibre bundle which connects a lens, arranged at the distal end, to the ocular, and a further light guide serving for illumination, and channels through which liquid can be drawn off by suction, water or air can be introduced and instruments can be inserted, for example for the removal of tissue samples.

A supply part is usually connected to the head via a supply tube which likewise contains, protected by a plastic sheath, a number of channels which can be connected to the channels in the insertion tube, on which supply part the said channels and the light guide serving for illumination open into attachments for the supply of water, air and light and for the removal of liquid by suction. Head part, insertion tube, supply tube and supply part are surrounded by an envelope, which consists of the housings of the head part and supply part and the sheaths of the insertion tube and supply tube and which encloses a continuous inner space containing both the channels and light guide mentioned as well as the delicate ocular. Also arranged on the supply part is a pressure test attachment which forms a connection to the inside of the endoscope.

The cleaning of endoscopes, which must be carried out very thoroughly for reasons of hygiene and must include disinfecting, is extremely involved and usually comprises a number of cleaning stages in which at least the insertion tube is exposed to a cleaning liquid under pressure. In a known method of the generic type (CH-A-675 064) the head part of the endoscope is therefore protected by a foam-filled housing, into the inside of which compressed air is fed. By this means, cleaning liquid cannot penetrate into the endoscope at the head part. However, if the insertion tube has a leak, and it is mainly the lower end thereof which is particularly susceptible to leaks, cleaning liquid can nevertheless penetrate into the inside of the endoscope and damage the ocular of the expensive instrument. One further disadvantage is that the head part is not cleaned.

It is also known to pump the endoscope up, using a hand pump, via the pressure test attachment prior to cleaning and in this way to detect any leaks. However, this method is not very reliable, mainly because very small leaks are rarely detectable, and affords no certainty against leaks appearing or increasing in size during cleaning, which can easily happen, particularly since the endoscope usually needs to be treated with cleaning liquid at a relatively high temperature. In addition, the testing in this case is a separate procedure from the cleaning and is relatively time-consuming.

A proven cleaning apparatus of the generic type, whose use nevertheless necessitates a leakproofness test prior to cleaning, is known from the brochure "Wasch- und Desinfektionsautomat für Endoskope SME 2000" (Automatic washing and disinfection apparatus for endoscopes SME 2000) from the company Belimed AG, 5608 Stetten, Switzerland.

SUMMARY OF THE INVENTION

The object of the invention involves a method for the integrated testing and cleaning of endoscopes, in which method there is no risk of cleaning liquid penetrating into the inside of the endoscope even if very small, undetectable leaks are present and if leaks appear or increase in size in the course of the cleaning. A further object is to propose a suitable cleaning apparatus for carrying out the method.

The invention provides a method in which the testing is carried out at the start and preferably before each cleaning stage, and the cleaning is discontinued if relatively large leaks are detected. The endoscope is additionally protected against the damaging effects of relatively small leaks, as can also occur during cleaning. Damage due to penetration of cleaning liquid can therefore be ruled out with a high degree of certainty. The testing is carried out together with the cleaning in a program-controlled manner. It requires rarely any additional expenditure in terms of time and no human intervention or attention. In the cleaning apparatus according to the invention, both steps can be performed automatically.

BRIEF DESCRIPTION OF THE DRAWING

The invention will be explained in greater detail hereinbelow with reference to figures which represent only one exemplary embodiment, and in which.

DESCRIPTION OF THE PREFERRED EMBODIMENT

Figure 1A:
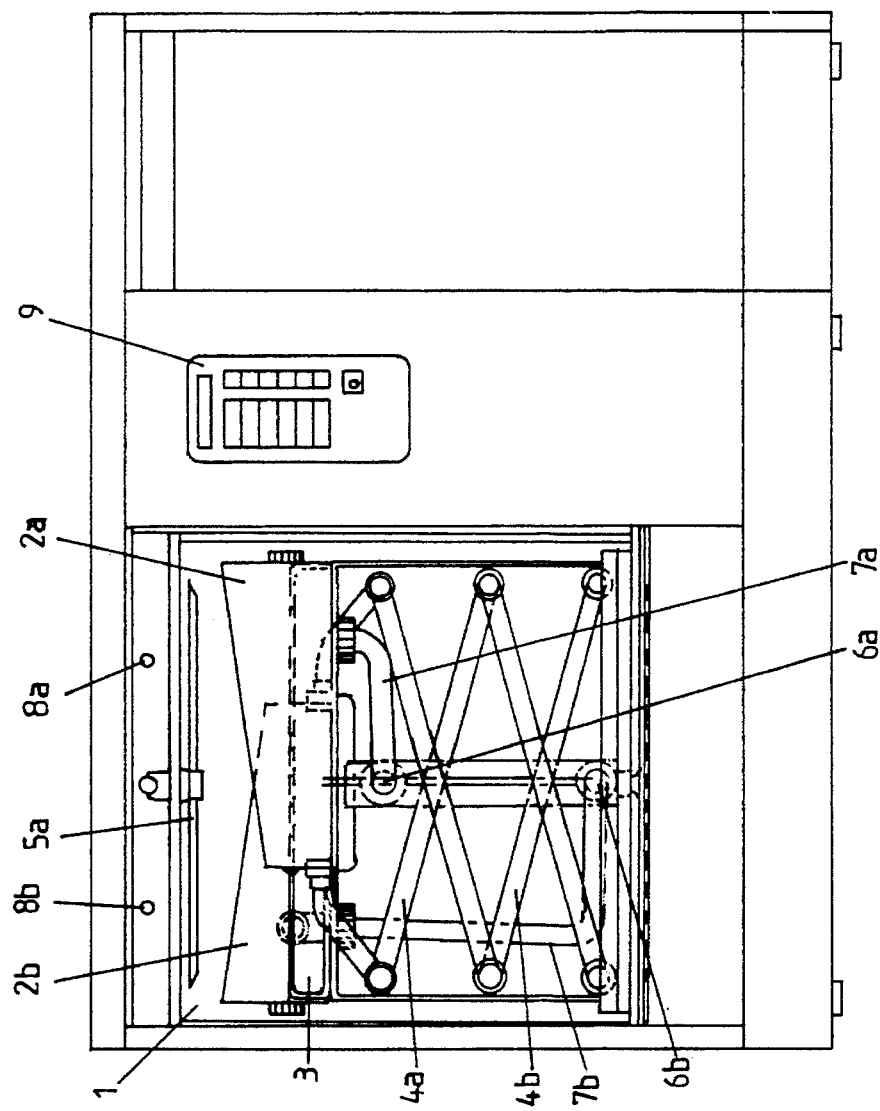
FIG. 1a shows a cleaning apparatus according to the invention in a front view, without door.
Figure 1B:
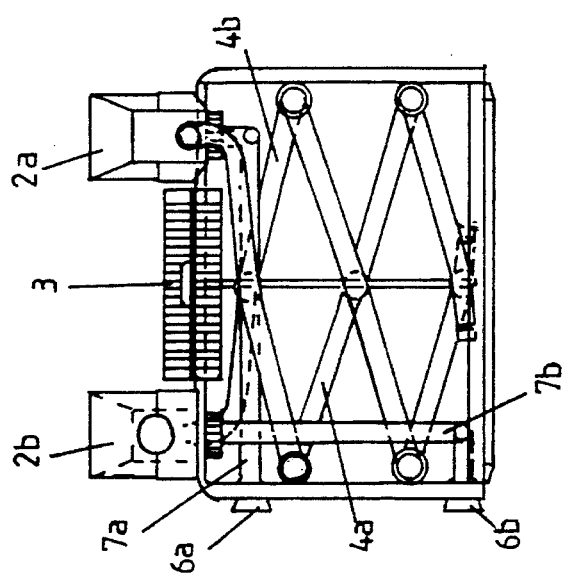
FIG. 1b shows the components of the cleaning apparatus according to FIG. 1a in a side view.

The cleaning apparatus has a cleaning chamber 1, in which two pressure chambers 2a, b made of stainless steel are incorporated, these consisting in each case of a lower part and of an upper part which can be swivelled open, and also a basket 3. Plastic pipes 4a, b of helical line configuration are attached to the pressure chambers 2a, b. Washing arms 5a, b are suspended in a rotatable manner in the vicinity of the lid and the base of the cleaning chamber 1. Arranged on the back wall are two pressurized water attachments 6a, b, which are connected to the pressure chambers 2a, b via pipes 7a, b, and also, directly underneath the lid, compressed air attachments 8a, b. A control panel 9 is arranged alongside the opening of cleaning chamber 1 on the front of the cleaning apparatus.

Figure 2:
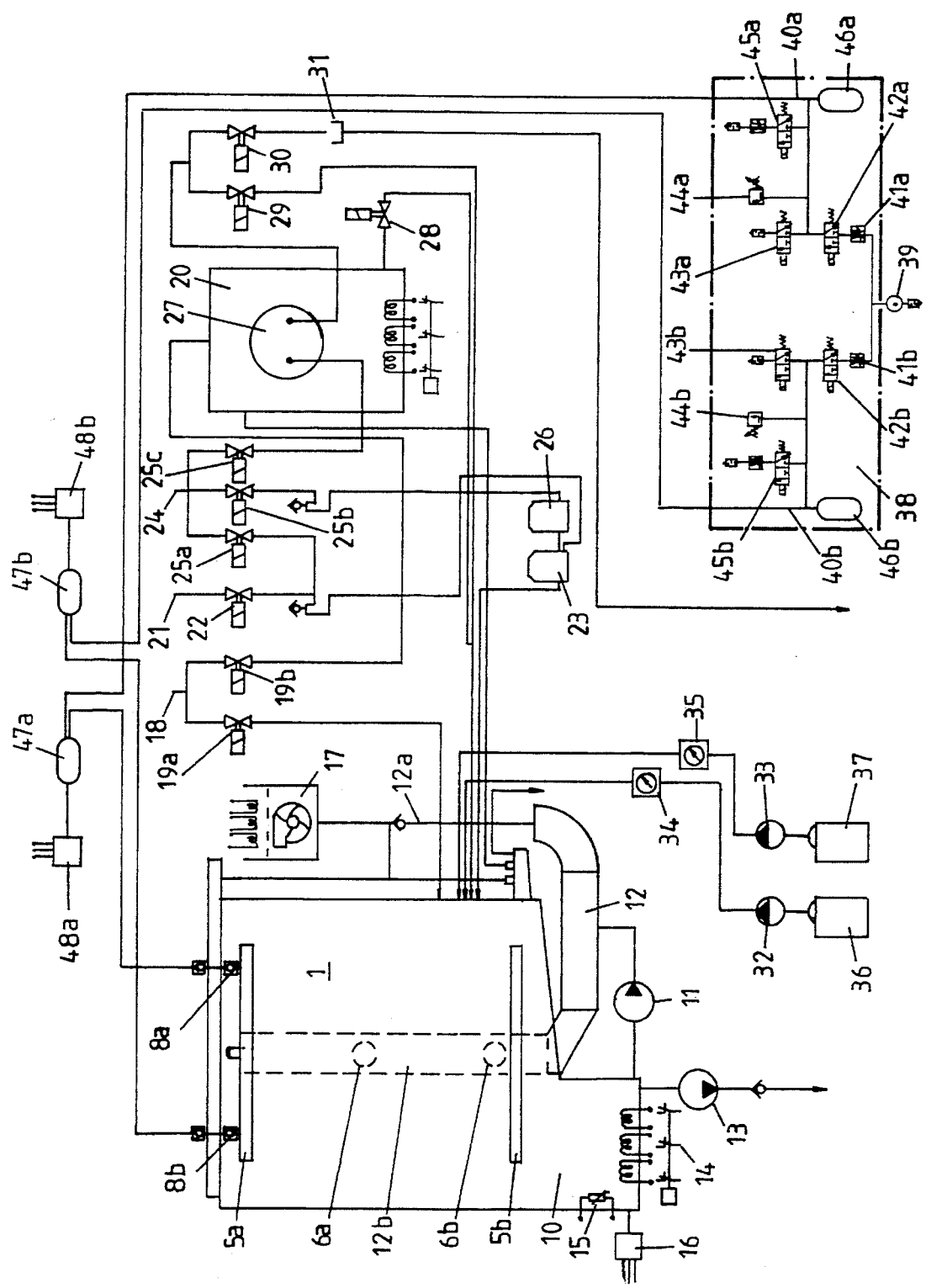
FIG. 2 shows a schematic representation of the construction of the cleaning apparatus according FIGS. 1a, 1b.

As can be seen from FIG. 2, the lower part of the cleaning chamber 1 is formed by a tank 10 which is connected via a circulation pump 11 to a collecting line 12, which supplies the washer arms 5a, b via a first branch 12a and supplies the compressed water attachments 6a, b via a second branch 12b. The tank 10 can be emptied by means of a suction pump 13. It is additionally provided with a heating arrangement 14 and a temperature sensor 15, and also with a pressure sensor 16 for monitoring its degree of filling. A heater fan 17 is connected to the first branch 12a of the collecting line 12.

The cleaning apparatus is supplied with water via three attachments. One attachment for demineralized water 18 is connected via a first valve 19a directly to the cleaning chamber 1 and via a second valve 19b to a boiler 20. A hot water attachment 21 is connected via a valve 22 and a decalcifier (ion exchanger) 23 likewise to the cleaning chamber 1, while a cold water attachment 24 is connected via a first valve 25a likewise to the decalcifier 23, via a second valve 25b to a regenerating salt storage unit 26, upstream of the decalcifier 23, and finally via a third valve 25c to a heat exchanger 27 which is arranged in the boiler 20. A line leads in each case through the boiler 20 and from the heat exchanger 27 via a valve 28 and 29, respectively, into the cleaning chamber 1, a further line additionally leading via a valve 30 to an outlet 31. A storage unit 36 for a cleaner and a storage unit 37 for disinfectant are likewise connected to the cleaning chamber 1 in each case via a pump 32 and 33, respectively, and a flow rate indicator 34 and 35, respectively.

The cleaning apparatus additionally has a compressed air unit 38 with a pump 39, which supplies the compressed air attachments 8a, b via two branches. The first branch has, downstream of the pump 39, a line 40a in which a throttle 41a and an admission valve 42a lie, and from which there branch a rapid venting valve 43a, a mechanical pressure relief valve 44a, with a response pressure of 500 mbar, a throttle outlet valve 45a and a compensating medium storage unit 46a for compensating for pressure variations. The second branch of the compressed air unit 38 is constructed in exactly the same way with a line 40b etc.

The line 40a leads to a compressed air storage unit 47a which is connected to the compressed air attachment 8a and is monitored by a pressure sensor 48a which controls the admission valve 41a and thus regulates the pressure. The line 40b is connected in an analogous manner to the compressed air attachment 8b via a compressed air storage unit 47b.

Figure 3:
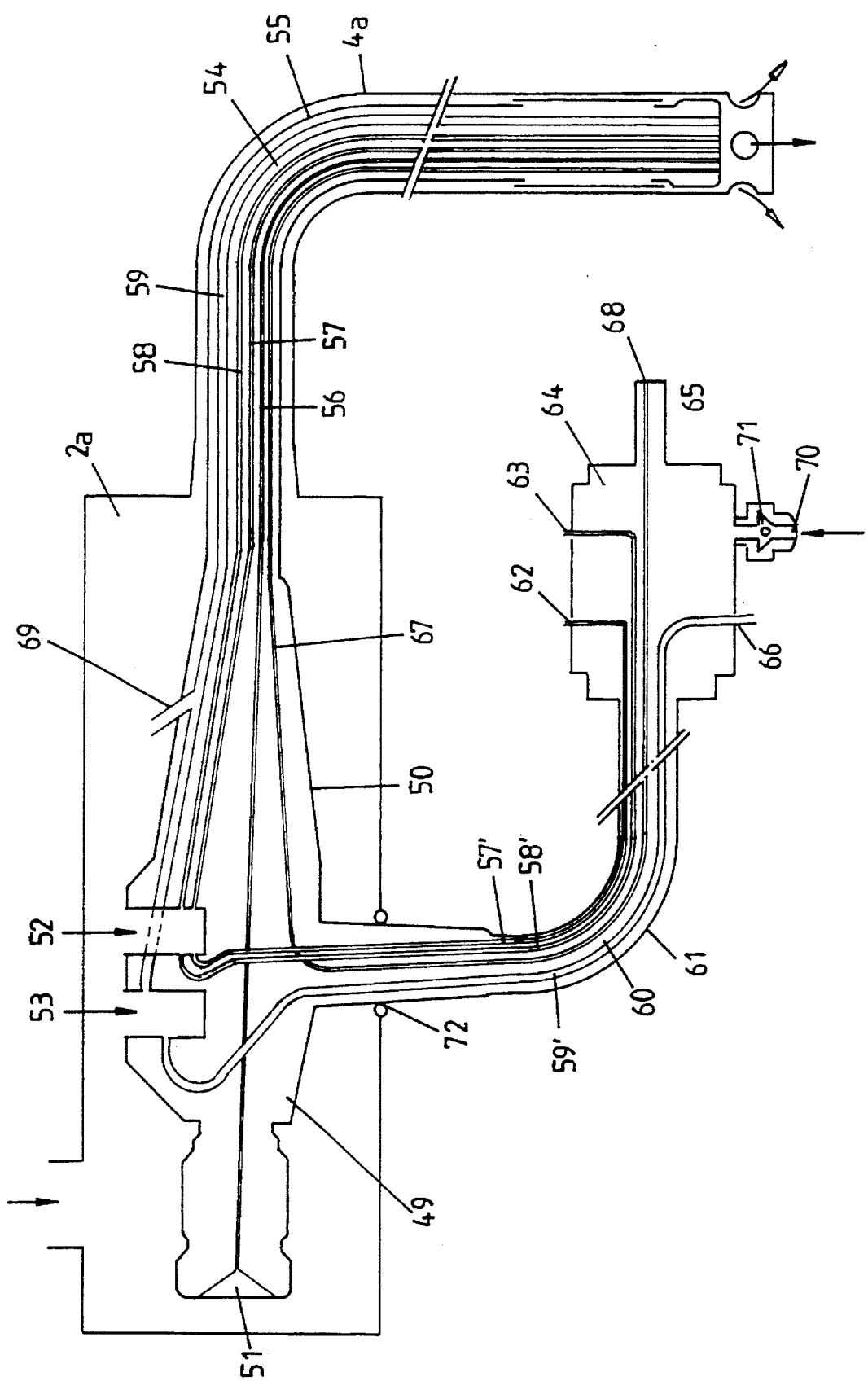
FIG. 3 shows diagrammatically a longitudinal section through an endoscope in a cleaning apparatus according to FIGS. 1a, 1b, 2, and FIGS. 4a and 4b show various parameters as functions of time during the implementation of the method according to the invention.

The endoscope shown in FIG. 3 has a head part 49 with a strong plastic housing 50, which lies in the pressure chamber 2a, and an ocular 51, a delicate component, which must not come into contact with water or any other cleaning liquid, and also, in openings 52 and 53 respectively, an air/water valve and a suction valve which, however, are removed for cleaning the endoscope and are therefore not shown. Secured on the head part 49 is a flexible insertion tube 54 which lies in the pipe 4a and contains, surrounded by a plastic sheath 55, a glass fibre bundle 56 which connects a lens at the distal end of the insertion tube 54 to the ocular 51, and also a water channel 57, an air channel 58 and a suction channel 59.

The water channel 57 and the air channel 58 open into the opening 52, from which continuations 57' and 58' of these channels emerge, these leading via a flexible supply tube 60, which is surrounded like the insertion tube 54 by a plastic sheath 61, to a water attachment 62 and an air attachment 63 on a supply part 64 with a strong plastic housing 65. The suction channel 59 and its continuation 59', which leads via the supply tube 60 to a suction attachment 66 on the supply part 64, similarly open into the opening 53. An optical fibre 67 runs from a light attachment 68 on the supply part 64 via the supply tube 60, the head part 49 and the insertion tube 54 as far as the distal end of the latter. On the head part 49 an attachment 69 branches off from the suction channel 59, through which attachment 69 various instruments can be led into the suction channel and through this to the distal end of the insertion tube 54.

The plastic sheath 55 of the insertion tube 54, the plastic housing 50 of the head part, the plastic sheath 61 of the supply tube 60, and the plastic housing 65 of the supply part 64 enclose a continuous inner space of the endoscope which, as has already been mentioned, also contains the ocular 51 and other delicate components. For the leakproofness testing, therefore, a pressure test attachment 70 is provided on the plastic housing 65 of the supply part 64, with a check valve 71 which forms a connection to the inside of the endoscope.

In order to clean an endoscope, the insertion tube 54 is introduced completely into the pipe 4a and the head part 49 is placed in the pressure chamber 2a. The supply tube 60, or more exactly an attachment piece for the latter on the head part 49, is passed outward in a sealed manner through a feed-through opening 72, which is sealed off by means of two rubber half-rings and consists of two semicircular recesses in the upper part and lower part of the pressure chamber 2a, and introduced into the basket 3. The pressure chamber 2a is then closed. The pressure test attachment 70 is connected in a sealed manner to the compressed air attachment 8a by means of a pressure test adaptor, a plastic tube, which is secured on it by means of an attachment piece. A second endoscope is introduced in the same way into the second pressure chamber 2b and is connected to the compressed air attachment 8b. The cleaning chamber 1 is then closed.

At the start of cleaning, demineralized water is passed into the boiler 20 via the attachment 18 and the valve 19b and is preheated to 85° C. The endoscope is then tested for leakproofness and the first cleaning stage, the actual cleaning, is initiated. In this context, reference is made to FIGS. 4a and 4b where the degree of filling of the tank 10 is shown at the bottom and the internal pressure of the endoscope (continuous lines) and the pressure of the cleaning liquid in the pressure chamber 2a (broken lines) above are shown in all cases as functions of time. While hot water coming from the hot water attachment 21 via the valve 22 and the decalcifier 23 is passed into the tank 10, which lasts approximately 100 sec, the pressure in the compressed air storage unit 47a and thus also in the endoscope is increased to a test pressure of 250 mbar by means of the pump 39 via the throttle 41a and the admission valve 42a. After a compensation time of approximately 5 sec, the air pressure in the compressed air storage unit 47a is established (first arrow in FIG. 4a). After a holding time of 30 sec, the measurement is repeated (second arrow). The same measurements are carried out in the compressed air chamber 47b, which has been brought at the same time to a pressure of 250 mbar via the second branch of the compressed air unit. If the pressure measured at the end of the holding time in both compressed air storage units 47a, b lies by less than a limit value of 30 mbar below the value established at the start of the holding time, the endoscope is recorded as being sufficiently leakproof and, therefore, the test result is regarded as being positive, and the first cleaning stage is begun by switching on the circulation pump 11, while cleaner is metered in from the storage unit 36 so that the pressure chambers 2a,b fill with cleaning liquid. The installation is designed in such a way that the pressure of the cleaning liquid lies at approximately 200 mbar. The internal pressure of the endoscope is in the meantime held at 250 mbar plus ±30 mbar by means of the pressure sensors 48a,b, which control the admission valves 42a,b. This pressure is tolerated satisfactorily by the endoscopes, whereas it would not be possible to exclude damage at pressures above 300 mbar.

The cleaning liquid is now circulated for approximately 10 minutes. It penetrates in each case into the openings 52, 53 of the endoscope and flushes through the water channel 57, the air channel 58 and the suction channel 59 and emerges at their distal ends and is passed back via the open end of the tube 4a and 4b, respectively, into the tank 10. Similarly, cleaning liquid flows along the outside of the insertion tube 54 through the pipe 4a and 4b, respectively, as a result of which not only is the plastic sheath 55 of the insertion tube 54 cleaned, but also suction is generated at the distal end of the insertion tube 54 as a result of the flow breaking off, which suction increases the pressure difference in relation to the openings 52, 53 and effects a good flushing-through of the channels at a comparatively low static pressure.

Cleaning liquid also flows from the openings 52, 53 through the continuations 57', 58' and 59' of the above mentioned channels and emerges at the water attachment 62, at the air attachment 63 and at the suction attachment 66 on the supply part 64. The supply tube 60 and the supply part 64 are cleaned on the outside by means of the rotating washer arms 5a,b, through which cleaning liquid is likewise pumped by the circulation pump 11.

Towards the end of the cleaning stage, during which the boiler 20 has been heated to a disinfection temperature of 93° C., the circulation pump 11 is shut off and the tank 10 is emptied via the suction pump 13, while at the same time compressed air from the compressed air storage units 47a,b and thus the endoscopes is let off through the throttle outlet valves 45a,b and the pressure is reduced.

In principle, the next cleaning stage, the rinsing, takes place, including the preceding testing of the endoscope, in a completely analogous manner to the first stage, except that no cleaner is added and the circulation pump 11 runs for only approximately 3 min.

The next cleaning stage too, the disinfection, which is also preceded by an endoscope testing, as described, differs from the preceding stages only in the preparation of the cleaning liquid and the duration. Cold water is passed into the tank 10 from the cold water attachment 24 via the valve 25c, the heat exchanger 27, where it is heated in the boiler 20 with cooling of the demineralized water, and the valve 29, and disinfectant is metered in from the storage unit 37. During the disinfection cold water is furthermore passed through the heat exchanger 27 and via the valve 30 to the outlet 31, as a result of which the content of the boiler 20 is cooled to below 55° C. During disinfection, the circulation pump 11 runs for somewhat more than 8 min.

For the last cleaning stage, the rinsing clean, the demineralized water is passed from the boiler 20, which was held at 93° C. for approximately 10 min and thus disinfected and then cooled to below 55° C., since higher temperatures are badly tolerated by endoscopes, via the valve 28 into the tank 10 and circulated for approximately 2 min. Otherwise, the rinsing clean, including the preceding endoscope testing, takes place exactly as the preceding cleaning stages. Finally, the endoscopes are dried by hot air issuing from the heater fan 17. The cleaning lasts approximately 40 min.

Of course, the cleaning described here represents only one example. The cleaning program can be adapted to the requirements and the circumstances and can be varied. The only respect in which nothing is altered is in the basic sequence of a cleaning stage, with preceding endoscope testing by building up an internal pressure in the endoscope, and subsequently circulating the cleaning liquid, while simultaneously maintaining the internal pressure above the pressure of the cleaning liquid.

If, for example, the endoscope to be cleaned reveals a large leak in the pressure chamber 2b, then the test pressure of 250 mbar in the endoscope and, consequently, in the compressed air storage unit 47b is not reached within a test interval of 5 min prior to the first cleaning stage. The circulation pump 11 is not set into operation and the cleaning is discontinued. An error message appears on the control panel 9.

FIGS. 4a and 4b show the case in which, during cleaning, a leak appears and increases in size in the endoscope being cleaned in the pressure chamber 2a. During the first cleaning stage, the actual cleaning, the endoscope is still leakproof; only towards the end do the air pressure variations, which are increasing but still lie appreciably below 30 mbar, indicate that the endoscope is losing air and the compressed air storage unit 47a must be frequently topped up. In the test prior to rinsing out, a pronounced pressure drop occurs during the holding time of 30 sec, which pressure drop is smaller, however, than the limit value of 30 mbar. This points to a relatively small leak. The pressure losses can be compensated without difficulty from the compressed air unit. The cleaning stage progresses normally, but the pressure in the compressed air storage unit 47a fluctuates significantly as a result of the losses and the topping-up, which is triggered by the pressure sensor 48a controlling the admission valve 42a.

In the test preceding the disinfection, a pressure drop of more than 30 mbar occurs during the holding time. This points to a relatively large leak, and the result of this is that the circulation pump 11 is not switched on and the filling of the tank 10 is discontinued. The latter is emptied via the suction pump 13. The compressed air is let off via the throttle outlet valves 45a,b and the cleaning is discontinued with an error message, without it having been possible for the cleaning stage to be initiated.

I claim:

1. A method for program-controlled testing and cleaning of an endoscope comprising the steps of placing the endoscope inside a cleaning chamber, and testing the endoscope by conveying compressed gas into the inside of the endoscope via a pressure test attachment of the same while checking whether the internal pressure of the endoscope reaches a test pressure, terminating the testing and cleaning program if the test pressure has not been reached at the end of a test interval, otherwise discontinuing gas supply and checking whether the internal pressure drops by more than a limit difference during a holding interval, terminating the testing and cleaning program if the internal pressure has dropped by more than the limit difference, otherwise advancing to a cleaning stage where the endoscope is exposed to a cleaning liquid while an internal pressure lying above the pressure of the cleaning liquid is maintained in the endoscope.

2. A method according to claim 1 where, during a cleaning stage, an internal pressure not lower than the test pressure by more than the limit difference is maintained in the endoscope and the pressure of the cleaning liquid does not exceed a maximum value lying below the test pressure by more than the limit difference.

3. The method of claim 2, where after the internal pressure of the endoscope has reached the test pressure within the test interval, by determining whether, during a holding interval, the internal pressure of the endoscope falls by more than a limit value without further supply of compressed gas.

4. A method according to claim 1 comprising several cleaning stages where each cleaning stage is preceded by a testing of the endoscope.

5. The method of claim 4, further maintaining during the cleaning stage an internal pressure corresponding at least to the difference between the test pressure and the limit value in the endoscope, and controlling the pressure of the cleaning liquid during the cleaning stage so as not to exceed a maximum value which is smaller than the said difference.

6. The method according to claim 4, comprising further step of using cleaning liquids of different temperatures in the various cleaning stages.

7. The method of claim 6, further repeating the cleaning stages but each cleaning stage is preceded by a testing of the endoscope.

8. The method according to claim 1, comprising the further step of maintaining the test pressure between 230 mbar and 300 mbar.

9. The method of claim 8, further using cleaning liquids of different temperatures in the various cleaning stages.

10. The method according to claim 1, comprising the further step of maintaining the limit value between 25 mbar and 50 mbar.

11. The method of claim 10, maintaining the test pressure between 230 mbar and 300 mbar.

12. The method according to claim 1, comprising the step of maintaining the length of the holding interval between 20 sec and 60 sec.

13. A method for program-controlled testing and cleaning of an endoscope with a head part, an insertion tube and a pressure test attachment, comprising the steps of inserting the head part and the insertion tube of the endoscope into a pressure chamber and into an open-ended pipe adjoining the pressure chamber, conveying compressed gas into the inside of the endoscope via the pressure test attachment of the same while checking whether the internal pressure of the endoscope reaches a test pressure, terminating the testing and cleaning if the test pressure has not been reached at the end of a test interval, otherwise discontinuing gas supply and checking whether the internal pressure drops by more than a limit difference during a holding interval, terminating the testing and cleaning if the internal pressure has dropped by more than the limit difference, otherwise advancing to a cleaning stage where a cleaning liquid is supplied under pressure to the pressure chamber while an internal pressure lying above the pressure of the cleaning liquid is maintained in the endoscope.

14. The method of claim 12, maintaining the limit value between 25 mbar and 50 mbar.

* * * * *